United States Patent [19]
Soukup et al.

[11] Patent Number: 5,609,622
[45] Date of Patent: Mar. 11, 1997

[54] IMPLANTABLE ELECTRODE WITH CONDUCTIVE POLYTETRAFLUOROETHYLENE ELECRODE

[75] Inventors: Thomas M. Soukup; Richard A. Staley, both of Flagstaff, Ariz.

[73] Assignee: W. L. Gore & Associates, Inc., Newark, Del.

[21] Appl. No.: 571,580

[22] Filed: Dec. 12, 1995

Related U.S. Application Data

[63] Continuation of Ser. No. 14,882, Feb. 1, 1993, abandoned.
[51] Int. Cl.$^6$ ........................................... A61N 1/05
[52] U.S. Cl. ........................................... 607/122
[58] Field of Search ........................... 128/642; 607/116, 607/115, 119, 122, 123, 125–128

[56] References Cited

U.S. PATENT DOCUMENTS

| | | |
|---|---|---|
| 3,953,566 | 4/1976 | Gore . |
| 4,030,509 | 6/1977 | Heilman et al. . |
| 4,033,355 | 7/1977 | Amundson . |
| 4,096,227 | 6/1978 | Gore . |
| 4,280,511 | 7/1981 | O'Neill .................................. 607/122 |
| 4,291,707 | 9/1981 | Heilman et al. . |
| 4,328,812 | 5/1982 | Ufford et al. ........................... 607/122 |
| 4,458,695 | 7/1984 | Peers-Trevarton ...................... 607/123 |
| 4,481,953 | 11/1984 | Gold et al. ........................... 607/123 X |
| 4,499,907 | 2/1985 | Kallok et al. . |
| 4,542,752 | 9/1985 | DeHaan et al. . |
| 4,559,951 | 12/1985 | Dahl et al. ........................... 607/122 X |
| 4,573,480 | 3/1986 | Hirschberg . |
| 4,576,174 | 3/1986 | Miyazaki et al. . |
| 4,641,656 | 2/1987 | Smits . |
| 4,662,377 | 5/1987 | Heilman et al. . |
| 4,690,155 | 9/1987 | Hess . |
| 4,827,932 | 5/1989 | Ideker et al. . |
| 4,840,186 | 6/1989 | Lekholm et al. . |

(List continued on next page.)

FOREIGN PATENT DOCUMENTS

| | | | |
|---|---|---|---|
| 491979 | 6/1992 | European Pat. Off. | ............... 607/122 |
| 0269095 | 6/1989 | German Dem. Rep. | ............... 607/122 |
| 3305271 | 9/1984 | Germany . | |
| 3640033 | 5/1988 | Germany | .............................. 607/122 |
| 656313 | 6/1986 | Switzerland . | |
| 2182566 | 11/1989 | United Kingdom . | |

OTHER PUBLICATIONS

D Santel et al., Implantable Defibrillator Electrode System: A Brief Review PACE vol. 8, Jan.–Feb. 1985, pp. 123–131.
Stokes K, Implantable Pacing Lead Technology, IEEE Engineering in Medicine and Biology Mag. 1990; 9(02):43–49.

*Primary Examiner*—Jeffrey R. Jastrzab
*Attorney, Agent, or Firm*—Wayne D. House

[57] ABSTRACT

An implantable electrode in the form a helically wound conductor having an electrically conductive polymeric layer coaxially surrounding and contacting the helically wound conductor, wherein the electrically conductive polymeric layer is electrically conductive in a dry state prior to implantation. Preferably, the electrode has two conductive portions, the additional second conductive portion being preferably located at the distal tip. The implantable electrode preferably incorporates an insulating portion wherein an additional length of the helically wound conductor is continuous with the remaining length of helically wound conductor coaxially covered by the electrically conductive polymeric layer. The insulating portion has a coaxial covering of impermeable polymeric electrically insulating material which is preferably silicone tubing. More preferably the coaxial covering of impermeably polymeric electrically insulating material has an additional exterior coaxial covering of porous PTFE for improved biocompatibility and flexibility. The porous PTFE is preferably porous expanded PTFE having a fibril length of less than 10 microns in order to substantially preclude tissue ingrowth and tissue attachment. The electrically conductive polymeric layer of the electrode is preferably made of porous expanded PTFE containing an electrically conductive filler, the porous expanded PTFE again having a fibril length of less than 10 microns.

19 Claims, 7 Drawing Sheets

U.S. PATENT DOCUMENTS

| | | |
|---|---|---|
| 4,972,846 | 11/1990 | Owens et al. . |
| 4,985,296 | 1/1991 | Mortimer, Jr. . |
| 5,016,646 | 5/1991 | Gotthardt et al. . |
| 5,087,242 | 2/1992 | Petelenz et al. . |
| 5,090,422 | 2/1992 | Dahl et al. . |
| 5,111,811 | 5/1992 | Smits . |
| 5,111,812 | 5/1992 | Swanson . |
| 5,115,818 | 5/1992 | Hollemen et al. . |
| 5,148,806 | 9/1992 | Fukui et al. . |
| 5,165,403 | 11/1992 | Mehra . |
| 5,191,901 | 3/1993 | Dahl et al. . |
| 5,330,520 | 7/1994 | Maddison et al. ............ 607/122 |

IMPLANTABLE ELECTRODE WITH CONDUCTIVE POLYTETRAFLUOROETHYLENE ELECRODE

This application is a continuation, of application Ser. No. 08/014,882 filed Feb. 1, 1993 now abandoned.

FIELD OF THE INVENTION

This invention relates to the field of implantable electrodes and in particular transvenous defibrillator leads and heart pacer sensing leads.

BACKGROUND OF THE INVENTION

Transvenous defibrillator leads are useful for the correction of ventricular tachycardia and ventricular fibrillation. Leads of this type are intravenously positioned so that the electrode portion of a lead is located within the right side of the heart. The lead may have only a single conductive electrode surface at or near the distal tip of the lead which is intended to be used in conjunction with an additional, separate and independent electrode such as a patch electrode located subcutaneously on the left side of the body. Alternatively, the transvenous defibrillator lead may incorporate two separate electrodes at or near the distal tip of the lead which may be used in conjunction to deliver electrical energy to the heart. More than two electrodes may be provided within the distal tip portion if it is desired to provide electrodes for sensing as well as for delivering electrical energy.

Conventional transvenous defibrillator leads use a helically wound wire to conduct the electrical energy from the connector at the proximal end of the lead to the electrode at the distal end. Multiple conductor wires typically are in the form of separate helically wound wires in coaxial relationship wherein each wire is separated from an adjacent wire by a tubular insulating layer. Alternatively they may be in the form of a co-linear helical winding wherein the individual wires are individually insulated prior to winding into a single helical form.

The conductive electrode surface is most commonly provided by leaving a length of the helically wound wire uninsulated and exposed to allow it to be exposed to the interior surface of the heart. While using the helically wound wire has the advantage of eliminating a connection between a separate electrode and the conductor wire, it has a fundamental disadvantage in that tissue grows into the exposed helically wound wire over time with the result that the lead can be extremely difficult to remove by the application of tension to the proximal end of the lead.

Various methods have been attempted to overcome this difficulty. For example, U.S. Pat. No. 5,090,422 describes the use of a porous covering for use over the electrode surface wherein the covering is made of a biocompatible material which may be an insulating material but becomes conductive by virtue of penetration of the material by conductive body fluids. The porous covering is of adequately small pore size to preclude substantial tissue ingrowth. Recommended materials include woven, porous polyurethane and porous polytetrafluoroethylene if used with a wetting agent or surface modifier.

SUMMARY OF THE INVENTION

The present invention is an implantable electrode which comprises a helically wound conductor having an electrically conductive polymeric layer coaxially surrounding and contacting the helically wound conductor, wherein the electrically conductive polymeric layer is electrically conductive in a dry state prior to implantation. The implantable electrode is primarily useful for transferring high levels of electrical energy for defibrillation to interior surfaces of a living heart, for example as the electrode portion of a transvenous defibrillator lead. Alternatively, the implantable electrode is also useful for transferring much lower levels of electrical energy, for example, sensing signal levels as required by pacing systems.

The implantable electrode is preferably connected to a source of electrical energy by an appropriate length of insulated wire. The helically wound conductor portion of the insulated wire is preferably continuous with the helically wound conductor that is coaxially covered by the electrically conductive polymeric layer and thereby forms the electrode surface that transfers energy to the heart. The helically wound conductor can therefore be said to have a first length portion that is coaxially covered by an electrically conductive polymeric layer, hereinafter termed the conductive portion, and a second length portion that is coaxially covered by an electrically insulating layer, hereinafter termed the insulating portion. The insulating layer coaxially covering the second length portion of the helically wound conductor is required to be made of an impermeable polymeric electrically insulating material such as silicone in order that the helically wound conductor is electrically isolated from contact with body fluids. Impermeable is used herein to describe a material that is substantially impervious to the transfer of ions across the thickness of the material. Preferably the insulating layer of impermeable polymeric electrically insulating material has an additional coaxial covering that provides the exterior surface of the insulated wire, the additional coaxial covering being porous polytetrafluoroethylene (hereinafter PTFE) of small pore size in order to substantially preclude tissue ingrowth into the void spaces of the porous PTFE. The function of the porous PTFE exterior surface of the insulated wire is to provide better biocompatibility and flexibility than is possible with the impermeable polymeric electrically insulating material alone.

The electrically conductive polymeric layer which comprises the coaxial covering of the conductive portion and is intended as the surface material that transfers electrical energy to the heart, is preferably made of porous PTFE containing a carbon filler. This material is electrically conductive in a dry state prior to implantation and also offers good biocompatibility. The electrically conductive polymeric layer may be of tubular form or alternatively may be in the form of a tape that is helically wrapped about the surface of the first length portion of the helically wound conductor.

The helically wound conductors are preferably MP35N stainless steel-nickel alloy and most preferably are wound from a wire made as a drawn, filled tube in the form of a silver core having an exterior surface coating of MP35N alloy. This type of conductor offers very good conductivity without exposing the silver conductor core to possible undesirable biological contact.

The implantable electrode of the present invention may be made with more than two electrodes by locating the electrodes sequentially along the length of the distal end of the implantable electrode. The electrodes are separated axially by lengths of insulating material such as silicone. The individual electrodes are supplied with electrical energy by individual helical wound conductors insulated from each other in either coaxial or co-linear relationship. The term co-linear describes a relationship wherein two or more individually insulated conductors are wound parallel to each other within the same helix.

Conventional connectors may be used to terminate the proximal end of the insulating portion for connection to a defibrillator energy source.

The porous PTFE used in various portions of the construction of the inventive implantable electrode is preferably porous expanded PTFE which for the purpose of this invention is herein defined as porous PTFE having a microstructure of nodes interconnected by fibrils. Porous expanded PTFE is described by and made according to the teachings of U.S. Pat. Nos. 4,187,390 and 3,953,566. The porous PTFE containing a carbon filler used for the surface of the conductive portion of the electrode is preferably porous expanded PTFE made according to the teachings of U.S. Pat. Nos. 4,096,227; 4,187,390; 4,985,296 and 5,148,806.

DETAILED DESCRIPTION OF THE INVENTION

Figure 1:
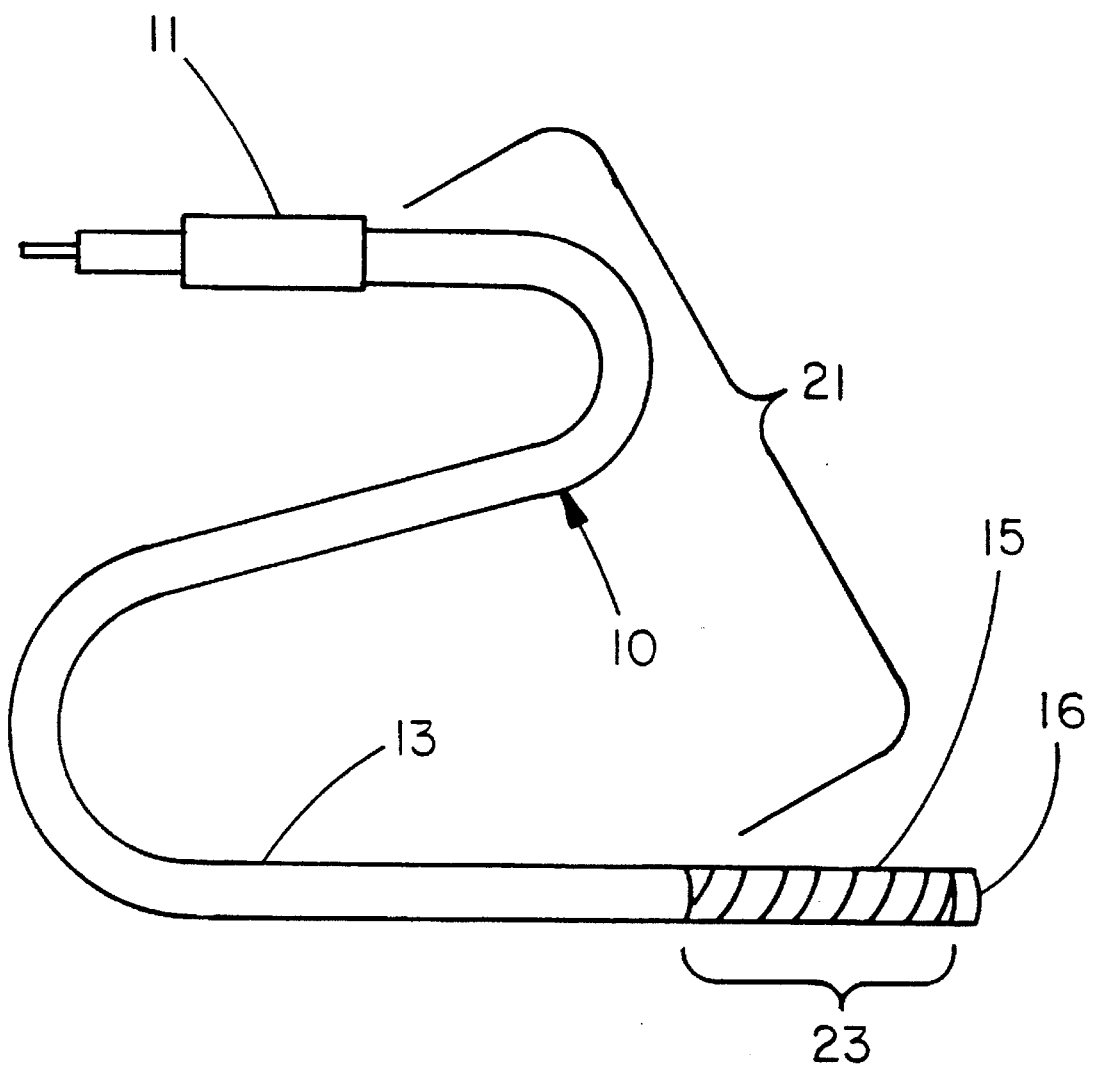
FIG. 1 describes a perspective view of an implantable electrode of the present invention incorporating a single conductive portion.
Figure 2:
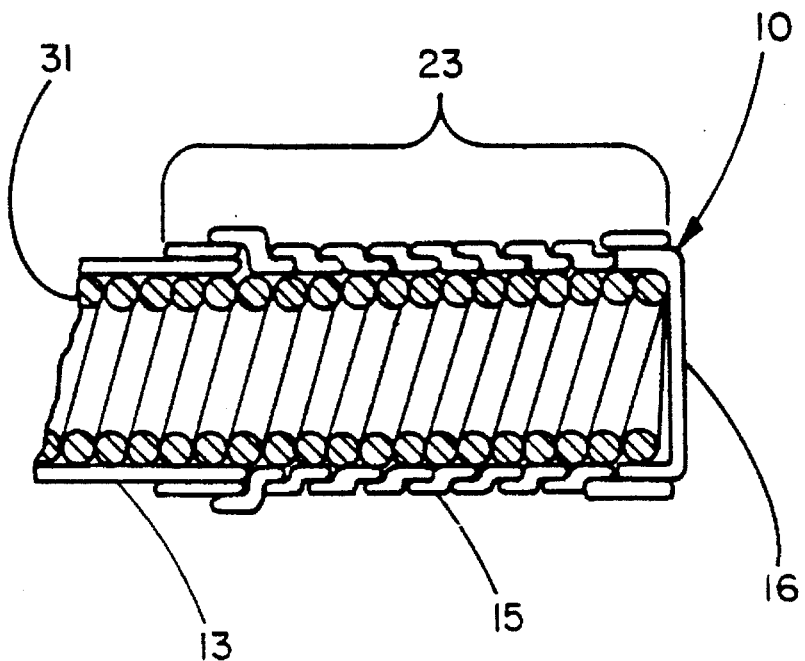
FIGS. 2 and 2A describe alternative cross sections of the implantable electrode of FIG. 1.

FIG. 1 shows the implantable electrode 10 of the present invention having an insulating portion 21, a conductive portion 23 and a conventional connector 11 terminating the proximal end of the electrode 10. As shown by the cross sectional view of FIG. 2, electrical energy is supplied to the conductive portion 23 by a helically wound conductor 31. The insulating material 13 coaxially covering the insulating portion 21 is comprised of a layer of impermeable polymeric electrically insulating material such as silicone tubing. The conductive portion 23 is comprised of an electrically conductive polymeric layer 15 which is electrically conductive in a dry state prior to implantation. The electrically conductive polymeric layer 15 is in direct electrical contact with the helically wound conductor 31 that supplies electrical energy to the conductive portion 23. This electrically conductive polymeric layer 15 is preferably comprised of a helically wrapped, porous PTFE tape containing a carbon filler wherein adjacent edges of the tape are overlapping. The porous PTFE containing a carbon filler is required to be of small pore size such as less than about 10 microns in order to limit tissue ingrowth. The distal end of this embodiment is covered by a cap 16 of either electrically conductive or electrically insulating material intended to close off the end of the tubular construction of the electrode 10.

The use of an electrically conductive polymeric material as the tissue contacting portion of the electrode is a significant improvement over conventional transvenous defibrillator leads relying on direct contact between an exposed portion of a helically wound conductor and living tissue. The difficulty with these conventional transvenous defibrillator leads is that over time tissue grows into the exposed portion of the helically wound conductor with the result that it becomes very difficult to withdraw the lead by applying traction to the proximal end. The conductive portion 23 of the present invention is either non-porous or alternatively of a porous material having a pore size adequately small to substantially preclude tissue ingrowth. Adequately small pore sizes are typically of 10 micron diameter or smaller. Porous PTFE and particularly porous expanded PTFE are preferred materials for the exterior surfaces of both the insulating portion 21 and conductive portion 23 because the porous PTFE is a chemically inert material with a long history of use in implantable medical devices and is well known to produce very little adverse tissue reaction. Additionally, the porous nature of the material allows the implantable electrode to be highly flexible and kink resistant.

The conductive porous PTFE for use as the electrically conductive polymeric layer that comprised the surface of the conductive portion 23 may be manufactured by uniformly distributing an electrically conductive filler throughout the porous PTFE during the process of making the porous PTFE layer. For example, if porous expanded PTFE is used, the electrically conductive particulate may be blended with the powdered PTFE resin prior to extrusion and expansion.

Pore size of porous expanded PTFE is generally described as a function of the fibril length of the material. The fibril length of porous expanded PTFE is measured as taught by U.S. Pat. No. 4,972,846 except that a sample magnification level greater than 100× may be necessary.

Figure 2A:
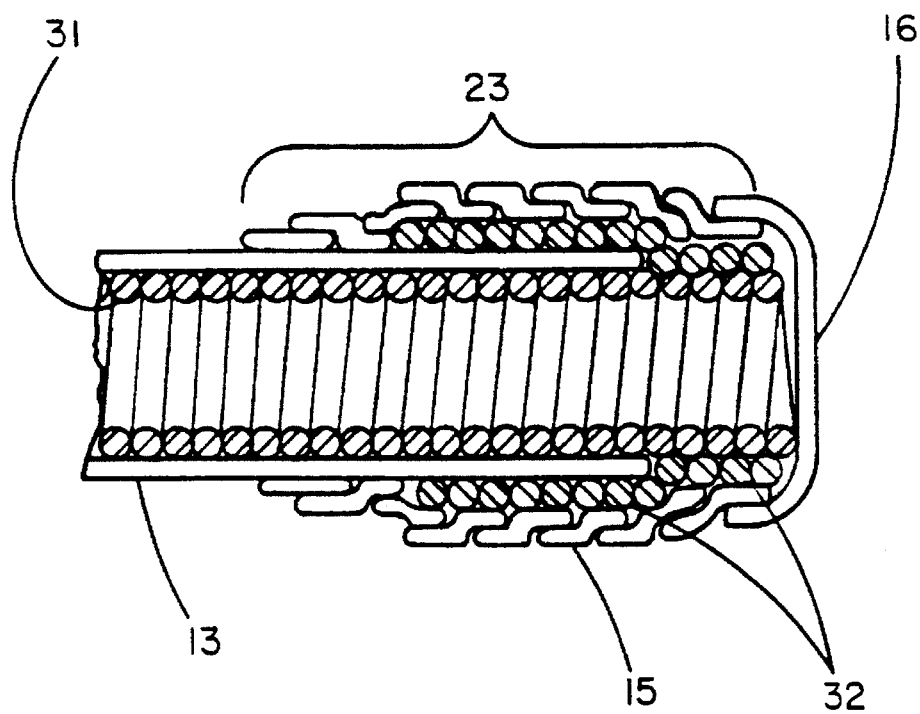

FIG. 2A describes an alternative embodiment wherein an additional relatively short length of a helically wound conductor 32 is fitted coaxially over the distal end of the first helically wound conductor 31 for the length of the conductive portion 23. At least a portion of the additional relatively short length of helically wound conductor 32 is in direct electrical contact with the first helically wound conductor 31. The use of the additional relatively short length of helically wound conductor 32 allows for a more corrosion resistant metal surface to which the electrically conductive polymer coaxial covering may be fitted. A preferred metal for the additional relatively short length of helically wound conductor 32 is titanium.

Figure 3:
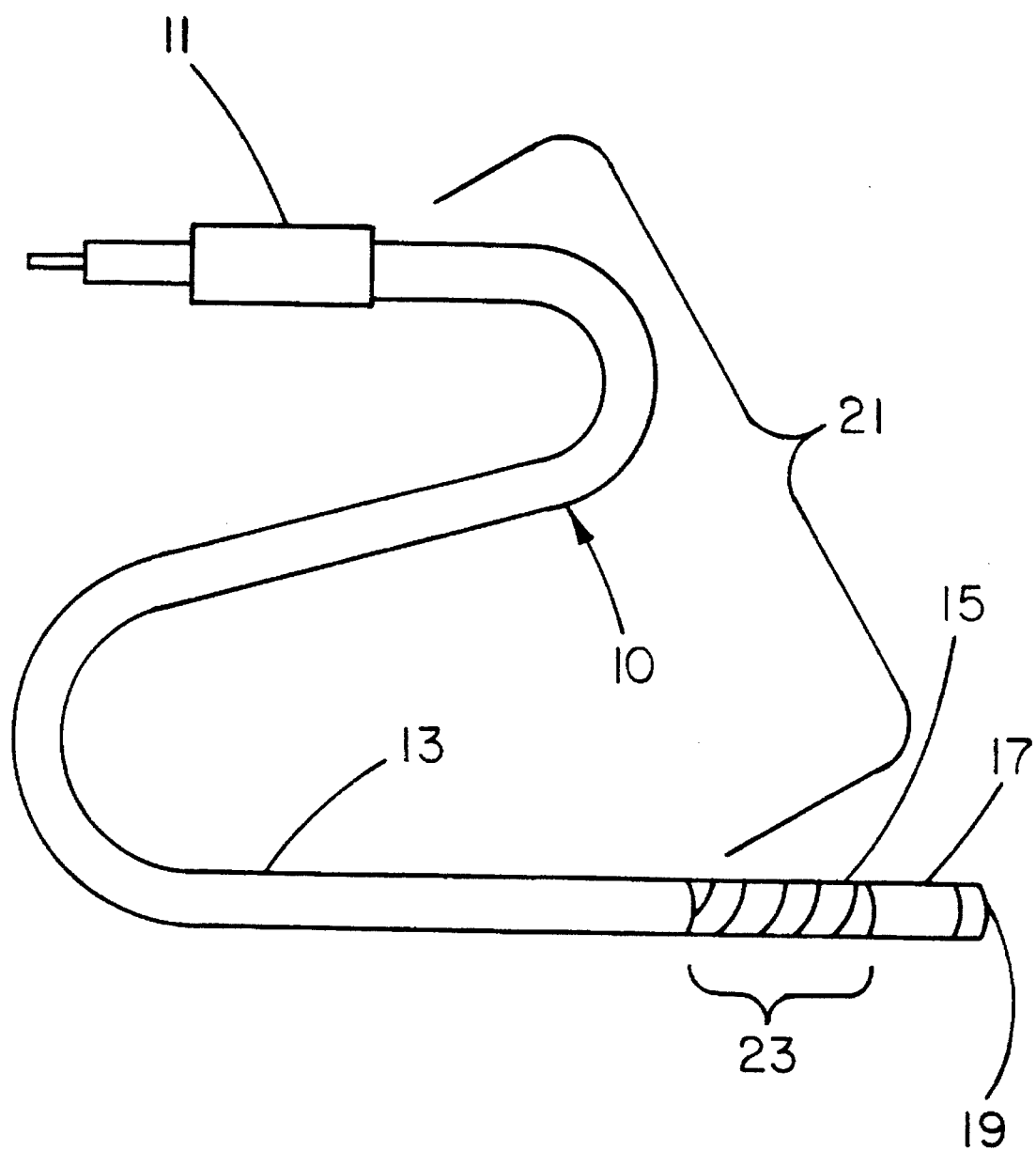
FIG. 3 describes a perspective view of a preferred embodiment of the implantable electrode incorporating two conductive portions.
Figure 4:
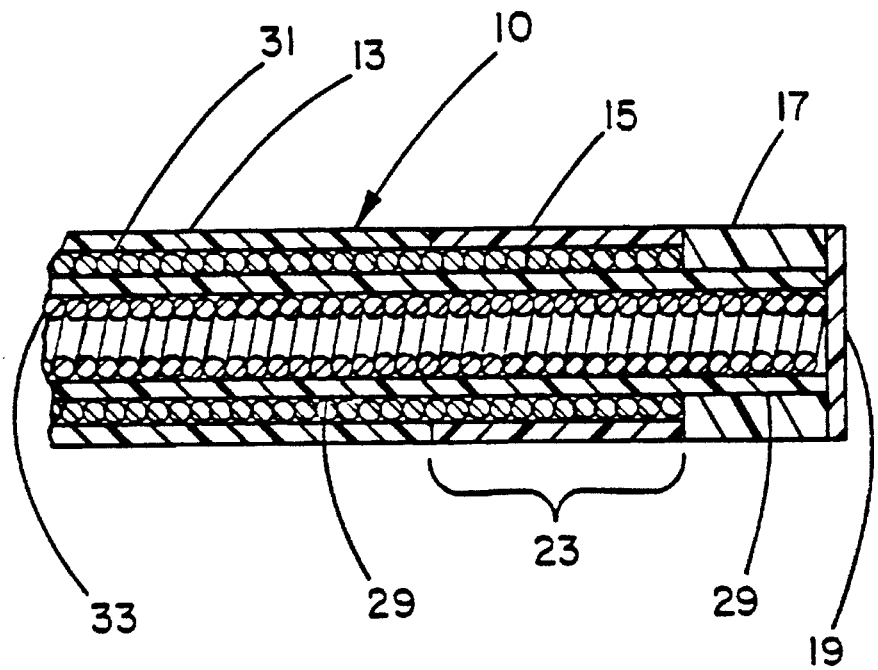
FIG. 4 describes a cross section of the implantable electrode of FIG. 3.

FIG. 3 shows a perspective view of a preferred embodiment of the implantable electrode of the present invention incorporating two conductive portions 23 and 19. FIG. 4 describes a cross section of this embodiment. The first conductive portion 23 is comprised as described previously of a layer 15 of electrically conductive polymeric material in contact with the first helically wound conductor 31. The second conductive portion 19 is located at the distal tip of the implantable electrode 10 and is preferably comprised of conventional metallic electrode materials such as platinum, carbon or titanium and may optionally incorporate a means for passively or positively attaching to a tissue surface, such as a barb, tine or screw thread. The second conductive portion 19 is connected to a second helically wound conductor 33 which is located coaxially within the lumen of the first helically wound conductor 31 and separated from the first helically wound conductor 31 by an impermeable tubular electrically insulating layer 29 which is preferably silicone tubing. The first and second conductive portions 23 and 19 are separated axially by a segment of impermeable polymeric electrically insulating material 17 at the surface of the distal end of the electrode 10.

Figure 4A:
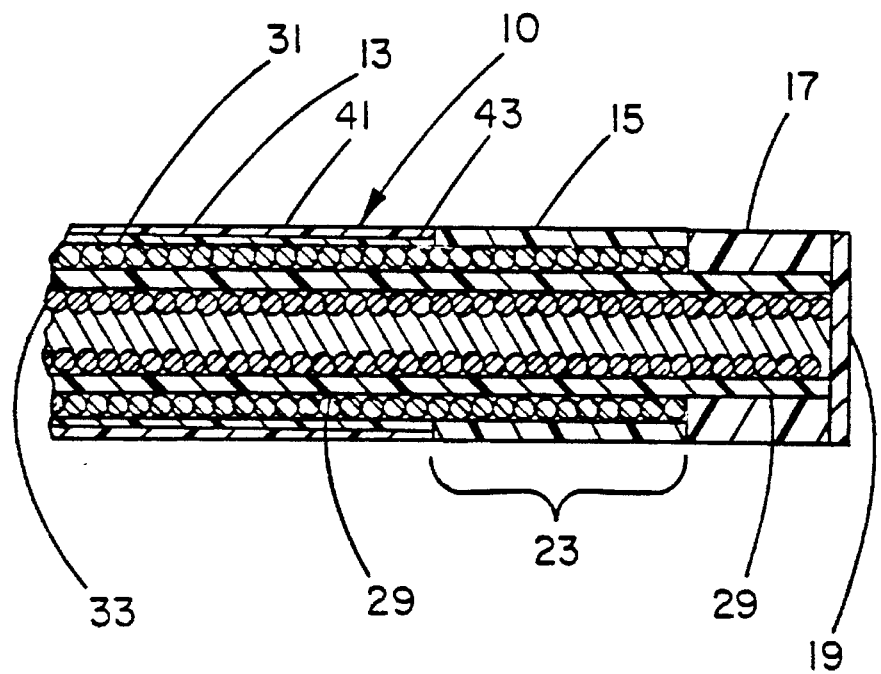
FIG. 4A describes an alternative embodiment to the implantable electrode shown by FIG. 4 wherein the insulating portion has an exterior layer of porous polymeric material with an underlying layer of impermeable polymeric insulating material.

FIG. 4A describes a cross section of an alternative embodiment to that described previously by FIG. 4. The insulating layer of FIG. 4A is comprised of separate inner and outer layers. Outer layer 41 is a coaxial covering of porous PTFE which is preferably porous expanded PTFE. The inner layer 43 is an impermeable polymeric electrically insulating layer. The use of porous PTFE for the exterior surface of the insulating portion 21 requires the use of an underlying impermeable polymeric electrically insulating layer 43. This is because body fluids will wet through the porous PTFE exterior coaxial covering thereby negating its electrical insulating value. This is true even for small pore size insulating materials, for example, porous expanded PTFE of less than 10 micron fibril length. The impermeable polymeric electrically insulating layer may be any suitable material and may also serve as an adhesive to secure the exterior porous insulating material to the underlying electrical conductor. Suitable materials include silicone tubing, silicone adhesive, and fluoropolymer tubing or tapes that may be helically wrapped about the surface of the electrical conductor.

Figure 5:
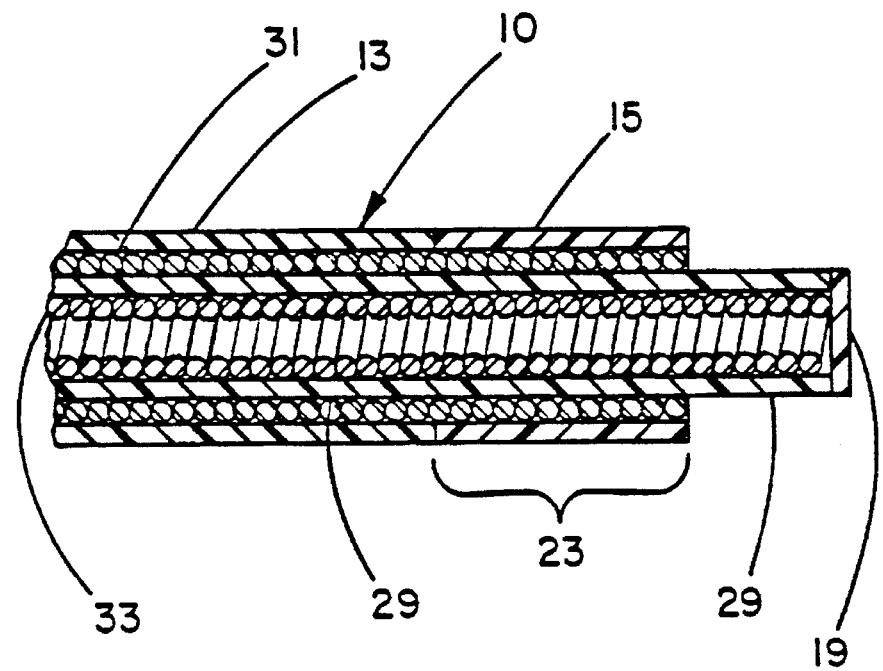
FIG. 5 describes a cross section of an alternative to the embodiment of FIGS. 3 and 4 incorporating a different tip construction.

FIG. 5 describes an alternative embodiment to those described previously by FIG. 3 and FIG. 4 wherein only the impermeable insulating tubular layer 29 separates the two electrodes at the surface of the implantable electrode 10. The additional layer of porous PTFE insulating material 17 described previously in the embodiment of FIG. 4 is omitted in this instance.

Figure 6:
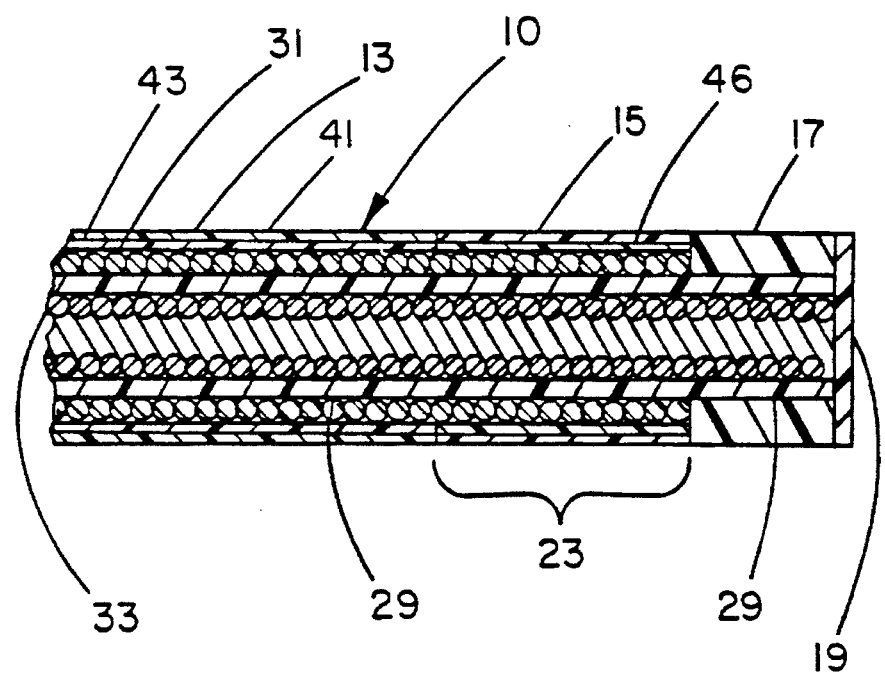
FIG. 6 describes a cross section of an alternative to the embodiment of FIG. 3 wherein the porous PTFE insulating material and the porous PTFE conductive material are secured to the surface of the helically wound conductor by a layer of an adhesive.

FIG. 6 shows a section of an alternative embodiment of the type described previously in FIGS. 3 and 4 wherein the porous PTFE insulating material 41 comprising the surface of the insulating portion 21 of the implantable electrode 10 is secured to the helically wound conductor 31 by a layer of adhesive 43 which may optionally serve as the impermeable electrically insulating layer if the adhesive characteristics meet those requirements. The adhesive is preferably a thermoplastic adhesive which is preferably a fluoropolymer and most preferably FEP. The adhesive securing the porous PTFE insulating material 41 may be either continuous as shown by layer 43 or alternatively may be discontinuous. If the adhesive layer is discontinuous, the use of a separate impermeable electrically insulating layer will be required. The electrically conductive polymeric material 15 may also be secured by a layer of adhesive 46 which should be discontinuous in order to allow for good electrical contact with the helically wound conductor 31. Alternatively the layer of adhesive 46 may be an electrically conductive adhesive and therefore may be applied continuously.

One such non-conductive adhesive is a dispersion of water, fluorinated ethylene propylene (hereinafter FEP) in the form of a particulate and a surfactant, available from DuPont (Wilmington, Del.) under the product name Teflon® FEP 120 Aqueous Dispersion. It has surprisingly been found that a thin layer of non-conductive polymeric adhesive produces good adhesion with little additional electrical resistance. Alternatively, conductive fillers such as carbon black may be added to this dispersion in order to make it electrically conductive. Six percent acetylene black (Shawinigan Acetylene Black, Gulf Canada Ltd., Montreal, Quebec, Canada) by weight of FEP has been found adequate to provide the adhesive with suitable electrical conductivity. This dispersion with and without acetylene black has been found useful to adhere the electrically conductive polymeric material of the electrode surface to the underlying helically wound conductor.

In another alternative, the porous PTFE may be made in sheet form having a layer of either continuous or discontinuous thermoplastic adhesive applied to one side of the porous PTFE sheet. After application of the adhesive to the PTFE sheet as will be described, the composite may then be slit into relatively narrow lengths of tape for subsequent helical wrapping about the conductor wire surface with the adhesive side of the composite contacting the conductor and the porous PTFE side facing outwardly. The helically wrapped conductor may then be heated to a temperature above the melt point of the thermoplastic adhesive to cause effective bonding of the composite tape to the conductor surface.

The process of making the porous PTFE material having a layer of either continuous or discontinuous thermoplastic adhesive comprises:

a) contacting a porous PTFE substrate, usually in the form of a membrane or film, with a layer, usually a film of a thermoplastic polymer;

b) heating the composition obtained in step a) to a temperature above the melting point of the thermoplastic polymer;

c) stretching the heated composition of step b) while maintaining the temperature above the melting point of the thermoplastic polymer; and d) cooling the product of step c).

Depending on the degree of stretching, the thermoplastic film can form a very thin, i.e., 9 micron or less thick, film on the surface of the expanded porous PTFE which is continuous and non-porous. Or, if the degree of stretching is great enough, the thermoplastic film will eventually rend and form rents. The rents are usually slit-like openings if the thermoplastic film is initially relatively thick, or are usually wider gaps or holes if the thermoplastic film is initially relatively thin. Such a film having gaps or holes is herein considered to be discontinuous. The thermoplastic film is preferably a fluoropolymer and most preferably FEP. The completed film may be slit into lengths of narrow tape for subsequent helical wrapping about the surface of an electrical conductor.

While FIG. 6 describes the porous PTFE insulating material 41 as being in the form of a continuous tube and the electrically conductive polymeric material 15 as being in the form of a helically wrapped tape, it is apparent that either continuous tubes or helically wrapped tapes may be used to provide the surface material for either the insulative portion 21 or the electrically conductive portion 23. Both the continuous tube covering and the helically wrapped covering may be secured as described by the thermoplastic adhesive.

Figure 7:
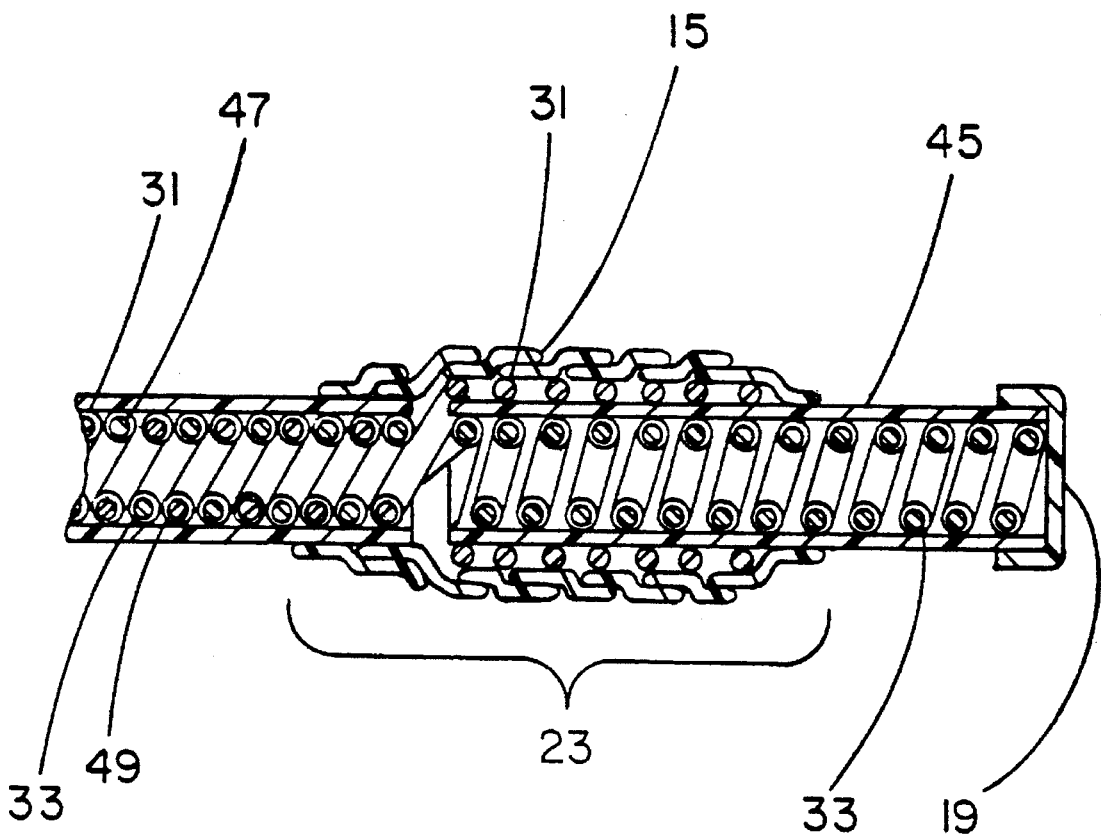
FIG. 7 describes a cross section of an alternative to the embodiment of FIG. 3 wherein the two helically wound conductors within the insulating portion are in co-linear relationship.

FIG. 7 describes a cross section of an alternative to the embodiment of FIG. 3 wherein the first 31 and second 33 helically wound conductors within the insulating portion are in co-linear relationship wherein the two insulated conductors are wound parallel to each other within the same helix.

The first 31 and second 33 helically wound conductors are separately insulated wherein the first conductor 31 has a layer of insulation 47 electrically isolating it from the second conductor 33 which has its own layer of insulation 49. At the beginning of the electrically conductive portion 23, the first 31 and second 33 helically wound conductors are separated into a coaxial relationship wherein the layer of insulation 47 has been removed from the first helically wound conductor 31, thereby allowing conductor 31 to be in direct electrical contact with conductive portion 23. The first 31 and second 33 helically wound conductors are insulated from each other beginning from the proximal end of the conductive portion 23 by a layer of impermeable polymeric electrically insulating material 45 coaxially covering the second helically wound conductor 33 which is in turn electrically connected to a distal tip electrode 19.

Figure 8:
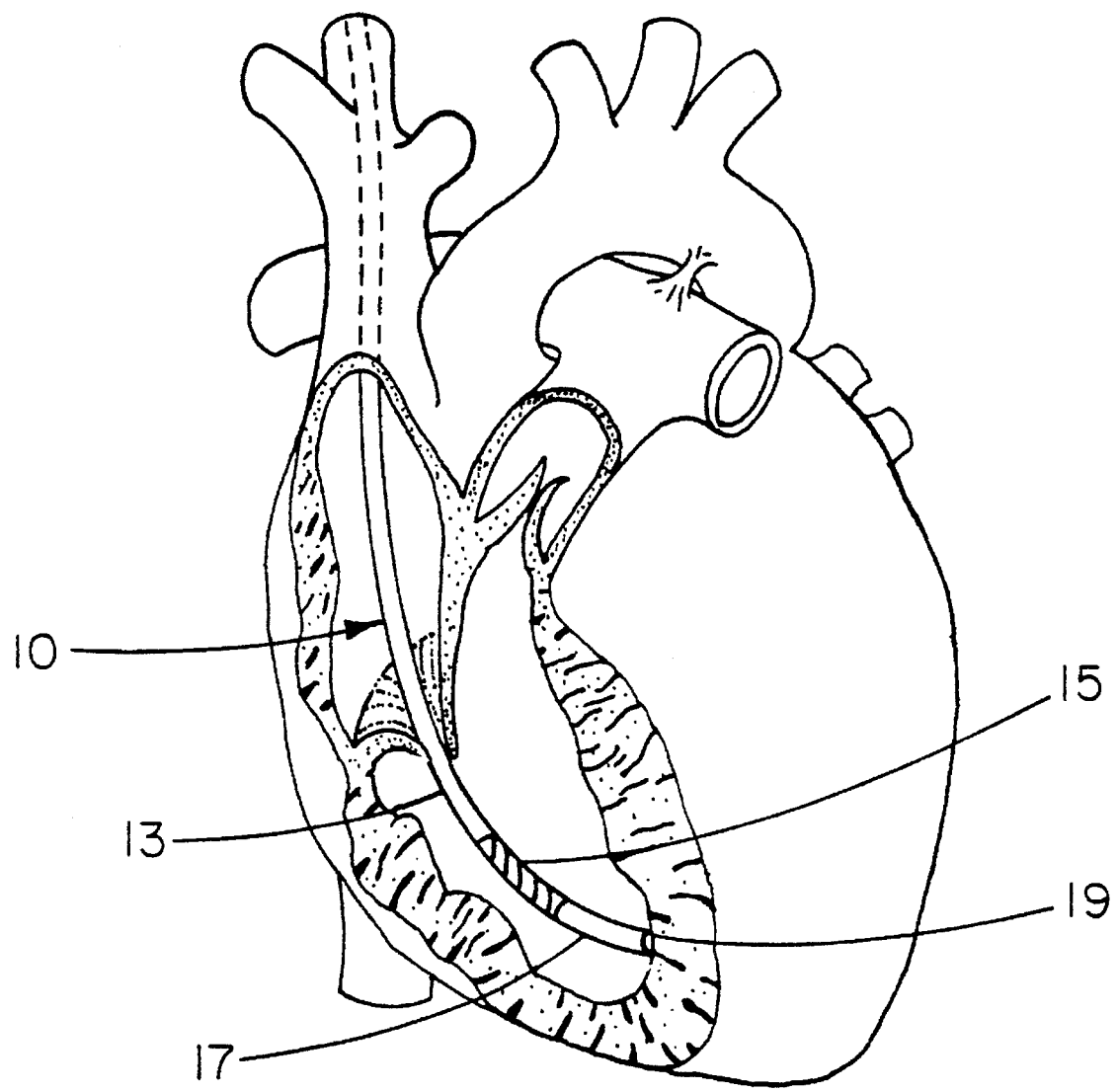
FIG. 8 is a schematic view of the implantable electrode of the present invention in use with a human heart.

FIG. 8 describes a schematic view of an implantable electrode of the present invention in use as a transvenous defibrillator lead with a human heart.

We claim:

1. An implantable electrode comprising at least one helically wound conductor having a first length portion wherein a layer of porous expanded polytetrafluoroethylene having a microstructure of nodes interconnected by fibrils and containing an electrically conductive filler coaxially surrounds and contacts the first length portion of the at least one helically wound conductor, wherein said porous expanded polytetrafluoroethylene has a mean fibril length less than about ten microns, wherein the layer of porous expanded polytetrafluoroethylene containing an electrically conductive filler is electrically conductive in a dry state prior to implantation, wherein the porous polytetrafluoroethylene containing an electrically conductive filler is in the form of a helically wrapped tape and wherein adjacent edges of the helically wrapped tape are in physical contact.

2. An implantable electrode according to claim 1 wherein the electrically conductive filler is a carbon filler.

3. An implantable electrode according to claim 2 wherein an additional relatively short length of a helically wound conductor coaxially covers and contacts a portion of the at least one helically wound conductor and is disposed between the at least one helically wound conductor and the layer of electrically conductive polymeric material.

4. An implantable electrode according to claim 1 wherein the at least one helically wound conductor has a second length portion continuously and electrically connected to the first length portion, and further has an insulating portion wherein the second length portion of the at least one helically wound conductor has a layer of impermeable polymeric electrically insulating material coaxially covering the second length portion of the at least one helically wound conductor.

5. An implantable electrode according to claim 4 wherein the porous polytetrafluoroethylene containing an electrically conductive filler is secured to the first length portion of the helically wound conductor by a discontinuous, non-conductive thermoplastic adhesive.

6. An implantable electrode according to claim 4 wherein the porous polytetrafluoroethylene containing an electrically conductive filler is secured to the first length portion of the helically wound conductor by an electrically conductive adhesive.

7. An implantable electrode according to claim 4 wherein the impermeable polymeric electrically insulating material is silicone.

8. An implantable electrode according to claim 4 wherein an additional relatively short length of a helically wound conductor coaxially covers and contacts a portion of the at least one helically wound conductor and is disposed between the at least one helically wound conductor and the layer of electrically conductive polymeric material.

9. An implantable electrode according to claim 4 wherein an additional helically wound conductor is coaxially disposed within the at least one helically wound conductor and electrically insulated from the at least one helically wound conductor by a layer of impermeable polymeric electrically insulating material coaxially disposed between the additional helically wound conductor and the at least one helically wound conductor, wherein the additional helically wound conductor is electrically connected to an electrically conductive component intended to transfer electrical energy to a tissue surface, the electrically conductive component being electrically insulated from the layer of electrically conductive polymeric material.

10. An implantable electrode according to claim 4 wherein an additional helically wound conductor is co-linearly disposed with the at least one helically wound conductor and electrically insulated from the at least one helically wound conductor by a layer of impermeable polymeric electrically insulating material coaxially covering the additional helically wound conductor and a second layer of impermeable polymeric electrically insulating material coaxially covering the at least one helically wound conductor, wherein the additional helically wound conductor is electrically connected to an electrically conductive component intended to transfer electrical energy to a tissue surface, the electrically conductive component being electrically insulated from the layer of electrically conductive polymeric material.

11. An implantable electrode according to claim 1 wherein an additional relatively short length of a helically wound conductor coaxially covers and contacts a portion of the at least one helically wound conductor and is disposed between the at least one helically wound conductor and the layer of electrically conductive polymeric material.

12. An implantable electrode according to claim 1 wherein the adjacent edges of the helically wrapped tape overlap.

13. An implantable electrode comprising at least one helically wound conductor having a first length portion wherein a layer of porous expanded polytetrafluoroethylene having a microstructure of nodes interconnected by fibrils and containing an electrically conductive filler coaxially surrounds and contacts the first length portion of the at least one helically wound conductor, wherein said porous expanded polytetrafluoroethylene has a mean fibril length less than about ten microns, wherein the layer of porous expanded polytetrafluoroethylene containing an electrically conductive filler is electrically conductive in a dry state prior to implantation and wherein the porous polytetrafluoroethylene containing an electrically conductive filler is secured to the first length portion of the helically wound conductor by a discontinuous, non-conductive thermoplastic adhesive.

14. An implantable electrode according to claim 13 wherein the discontinuous thermoplastic adhesive is a fluoropolymer.

15. An implantable electrode according to claim 14 wherein the fluoropolymer is fluorinated ethylene propylene.

16. An implantable electrode comprising at least one helically wound conductor having a first length portion wherein a layer of porous expanded polytetrafluoroethylene having a microstructure of nodes interconnected by fibrils and containing an electrically conductive filler coaxially surrounds and contacts the first length portion of the at least one helically wound conductor, wherein said porous expanded polytetrafluoroethylene has a mean fibril length less than that about ten microns, wherein the layer of porous expanded polytetrafluoroethylene containing an electrically conductive filler is electrically conductive in a dry state prior to implantation: wherein the at least one helically wound conductor has a second length portion continuously and electrically connected to the first length portion, and further has an insulating portion wherein the second length portion of the at least one helically wound conductor has a layer of impermeable polymeric electrically insulating material coaxially covering the second length portion of the at least one helically wound conductor and wherein the impermeable polymeric electrically insulating material has an exterior coaxial covering of porous polytetrafluoroethylene.

17. An implantable electrode according to claim 16 wherein the impermeable polymeric electrically insulating material is silicone.

18. An implantable electrode according to claim 16 wherein the exterior coaxial covering of porous polytetrafluoroethylene is porous expanded polytetrafluoroethylene.

19. An implantable electrode according to claim 18 wherein the exterior coaxial covering of porous expanded polytetrafluoroethylene has a mean fibril length less than about 10 microns.

* * * * *